United States Patent
Rothmann et al.

(10) Patent No.: US 12,286,665 B2
(45) Date of Patent: Apr. 29, 2025

(54) METHOD AND INSTRUMENTATION FOR SPATIAL MULTIOMICS USING SUMI-TECHNOLOGY

(71) Applicant: Miltenyi Biotec B.V. & Co. KG, Bergisch Gladbach (DE)

(72) Inventors: Thomas Rothmann, Langenfeld (DE); Robert Pinard, Lowell, MA (US); Hansueli Meyer, Acton, MA (US); Andreas Bosio, Cologne (DE); Heinrich Spiecker, Bielefeld (DE); Seiyu Hosono, Stoneham, MA (US); Ryan Hindman, Bergisch Gladbach (DE); Emily Neil, Bergisch Gladbach (DE); Chris Nehme, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 563 days.

(21) Appl. No.: 17/588,371

(22) Filed: Jan. 31, 2022

(65) Prior Publication Data

US 2022/0243260 A1 Aug. 4, 2022

(51) Int. Cl.
*C12Q 1/6841* (2018.01)
*C12N 15/10* (2006.01)
*C12Q 1/6804* (2018.01)
*C12Q 1/682* (2018.01)
*C12Q 1/6876* (2018.01)
*G01N 33/68* (2006.01)

(52) U.S. Cl.
CPC ....... *C12Q 1/6841* (2013.01); *C12N 15/1065* (2013.01); *C12Q 1/6804* (2013.01); *C12Q 1/682* (2013.01); *C12Q 1/6876* (2013.01); *G01N 33/6803* (2013.01); *G01N 2458/10* (2013.01)

(58) Field of Classification Search
CPC .................................................. C12Q 1/6841
See application file for complete search history.

(56) References Cited

U.S. PATENT DOCUMENTS

2021/0403992 A1* 12/2021 Pinard .................. C12Q 1/6869

FOREIGN PATENT DOCUMENTS

| WO | WO 2017081049 A1 | 5/2017 |
| WO | WO2017143155 A2 | 8/2017 |
| WO | WO2018045181 A1 | 3/2018 |
| WO | WO2019068880 | 4/2019 |

OTHER PUBLICATIONS

Andrew Payne et al., "In situ genome sequencing resolves DNA sequence and structure in intact biological samples", Feb. 26, 2021, Science, 371, pp. 1-14. Paper was published Dec. 30, 2020 online (Year: 2021).*
Daniel Gyllborg et al. "Hybridization-based in situ sequencing (HybISS) for spatially resolved transcriptomics in human and mouse brain tissue", Sep. 29, 2020, Nucleic Acids Research, 2020, vol. 48, No. 19, pp. 1-11. (Year: 2020).*
Yukie Kashima et al., "Single-cell sequencing techniques from individual to multiomics analyses", Exp Mol Med 52, pp. 1419-1427 (2020).Sep. 15, 2020 (Year: 2020).*
Richie E. Kohman et al., "Fluorescent in situ sequencing of DNA barcoded antibodies", Apr. 28, 2020, bioRxiv, pp. 1-7. (Year: 2020).*
Marco Mignardi et al., "Oligonucleotide gap-fill ligation for mutation detection and sequencing in situ", Jul. 19, 2015, Nucleic Acids Research, vol. 43, No. 22, pp. 1-12 (Year: 2015).*
"In-Situ Sequencing for RNA analysis in preserved tissue and cells," R. Ke, et al, Nature Methods, vol. 10 No. 9, Sep. 2013.
"Efficient In Situ Detection of mRNAs using the Chlorella virus DNA ligase for Padlock Probe Ligation" by Nils Schneider and Matthias Meier; Feb. 5, 2020—Cold Spring Harb.
"Highly multiplexed subcellular RNA sequencing in situ" by Lee et al., Science. Mar. 21, 2014; 343(6177): 1360-1363. doi:10.1126/science.1250212.
"Highly multiplexed subcellular RNA sequencing in situ" by Lee et al., Science. Mar. 21, 2014; 343(6177): 1360-1363.

* cited by examiner

*Primary Examiner* — Nancy J Leith
*Assistant Examiner* — Jessica D Parisi
(74) *Attorney, Agent, or Firm* — Jaquelin K. Spong

(57) ABSTRACT

Microscopy imaging that allow for multiple mRNAs, proteins and metabolites to be spatially resolved at a subcellular level provides valuable molecular information which is a crucial factor for understanding tissue heterogeneity as for example within the tumor micro environment. The current invention describes a method (SUMI-Seq) which combines the use of Spatial Unique Molecular Identifier in situ sequencing and in vitro sequencing of rolonies derived from rolling circle amplification from padlock oligonucleotides targeting portion of RNA or cDNA transcript at a subcellular level with less limitation in the amount of transcripts and the length of the sequence that can be analyzed. Apart from padlocks oligonucleotides, the SUMI-Seq method can also be applied using circular oligonucleotides to spatially resolve proteins and metabolites to provide multiomics results.

7 Claims, 8 Drawing Sheets

METHOD AND INSTRUMENTATION FOR SPATIAL MULTIOMICS USING SUMI-TECHNOLOGY

CROSS REFERENCE TO RELATED APPLICATIONS

This US nonprovisional application claims priority to EP 21155163.5, filed Feb. 4, 2021. This prior application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention relates to a method for sequencing and localizing RNA or c-DNA strands.

Padlock oligonucleotides have proven to be very successful in polymerizing short portion of nucleic acids to which it has been hybridized to. Most padlock approaches begin by reverse transcribing the target into cDNA.

Padlock methods are for example disclosed in "Highly multiplexed subcellular RNA sequencing in situ" by Lee et al., Science. 2014 Mar. 21; 343(6177): 1360-1363. doi: 10.1126/science.1250212 or "Efficient In Situ Detection of mRNAs using the *Chlorella* virus DNA ligase for Padlock Probe Ligation" by Nils Schneider and Matthias Meier; Feb. 5, 2020—Cold Spring Harbor Laboratory Press.

A comprehensive assay for targeted multiplex amplification of human DNA sequences is published by Sujatha Krishnakumar et al.; PNAS sent for review Feb. 19, 2008.

Further, WO2017143155A2 discloses multiplex alteration of cells using a pooled nucleic acid library and analysis thereof and WO2018045181A1 discloses Methods of generating libraries of nucleic acid sequences for detection via fluorescent in situ sequencing.

The published Padlock methods allow sequencing of DNA or RNA, but do not give any spatial information within a cell and tissue location the sequenced DNA or RNA origins from.

Microscopy imaging that allow for multiple mRNAs to be resolved at a single cell level provides valuable information regarding transcript amount and localization, which is a crucial factor for understanding tissue heterogeneity, the molecular development and treatment of diseases.

Fluorescence in situ hybridization (FISH)-based methods allow for transcripts to be directly labelled in tissue sections and for spatial information to be captured. However, the numbers of probes that can be used is limited and overlap of fluorescence signals is often an issue. Moreover, the optical resolution of confocal microscopy limits often are reached and therefore the amount of probes that can be detected concomitantly is reduced. SeqFISH+, is an approach that does not use probes already labelled with fluorophores but rather uses transcript-specific ones that contain barcode sequences which serve as target sites for fluorescently labelled secondary probes. The various target-specific probes are identified using secondary probes that bind to these barcode sites during sequential rounds of probing. By limiting the amount of probes that are detected by the secondary probes a limited amount are fluorescing and therefore the signal can be discernible. Multiple separated images are collected and aggregated computationally to create a composite high-resolution image without requiring high resolution instrument microscope.

However, although these approaches allow for the evaluation of several genes simultaneously, the sequence information of the transcript is not captured. Other methods based on single-cell RNA sequencing (scRNA-seq) can profile whole transcriptomes and capture the sequence information. However, the original location at the tissue or single cell level is often also missing. A method where both sequence and spatial information is be captured at a resolution approaching the single-cell remains a difficult challenge. Some approaches have used FISSEQ and BaristaSeq (another gap-filling padlock based approach to achieve that task with a limited read-length of about 15 bases).

Recently in situ genome sequencing (IGS) has been described as a method to simultaneously sequence and image genomes within a sample. This method describes a workflow to localize unique molecular identifiers (UMIs) by short read in situ sequencing followed by amplicon dissociation, PCR and ex situ sequencing of amplicons associated to genomic sequences with UMIs by paired-end sequencing published by A. C. Payne et al., Science 10.1126/science.aay3446 (2020), first online release 31 Dec. 2020.

SUMMARY OF THE INVENTION

Object of the invention is a method to obtain the spatial location and sequence information of a target sequence in a sample comprising at least one RNA or c-DNA strand comprising the steps
 a. providing an oligonucleotide having a 5' and a 3' end combined by 50-1000 nucleic acids that are complementary to the at least one RNA or c-DNA strand of the sample
 b. hybridizing the oligonucleotide at the 5' and the 3' ends to complementary parts of the at least one RNA or c-DNA strand to create a padlock with a gap between the 5' and the 3' end of the padlock
 c. filling the gap of the padlock with the complementary nucleic acids as target sequence and ligate them to generate a single strand circular template
 d. multiplying the single strand circular template by a polymerase capable of rolling circle amplification into a plurality of DNA concatemers thereby forming rolonies characterized in providing the oligonucleotide with at least one spatial unique molecular identifier (SUMI) comprising at least 2 nucleic acids
 e. determining the spatial location of the rolonies by in situ sequencing of the SUMI
 f. collecting the rolonies after in situ sequencing and transfer them for in vitro sequencing
 g. determining the sequence of the SUMIs and the target sequence by in vitro sequencing of the rolonies
 h. linking the target sequence of the rolonies with the spatial location obtained from in situ sequencing via the sequence of the SUMIs.

The method of the invention can be further used to obtain the spatial location of proteins is a sample.

Another object of the invention is a method for spatial single cell protein expression mapping comprising the steps
 a. providing a circular oligonucleotide comprising a barcode tag which is linked to antibody b. binding of the antibody to the protein in the sample
c. multiplying the single strand circular template by a polymerase capable of rolling circle amplification into a plurality of DNA concatemers forming a rolony characterized in
providing the oligonucleotide with at least one spatial unique molecular identifier (SUMI) comprising at least 2 nucleic acids
d. determining the spatial localisation of the SUMI by in situ sequencing.
e. collecting the rolonies after in situ sequencing and transfer them for in vitro sequencing
f. determining the sequence of the SUMIs and the target sequence by in vitro sequencing of the rolonies
g. linking the barcode-tag sequence of the rolonies via the SUMI to the spatial location obtained from in situ sequencing All embodiments and variants of the method to obtain the spatial location and sequence information of a target sequence in a sample comprising at least one RNA or c-DNA strand can also be applied in the method for spatial single cell protein expression.

Preferable, the spatial unique molecular identifier (SUMI) comprises 2-30, more preferable 4-14 nucleic acids)

The target sequence includes at least the nucleic acids filling in the gap of the padlock as defined in step c, but may also include the sequence of the region of the oligonucleotides providing the hybridisation to the DNA/RNA, i.e. the 5' and 3' ends of the oligonucleotide.

In the present invention, after the transfer of the rolonies in step f), the plurality of concatemers can also be digested into singlets, circularized and subjected to a second round of rolonization to generate daughter rolonies which contain the same information. The digestion to singlets may be achieved by sonication or enzymatic digestion. Enzymatic digestion may be targeted by a restriction enzyme where the binding site has been included in the padlock design, or other means of cleaving without modification of padlock design (e.g. incorporation of uracil and Uracil-N-Glycosylase treatment). Instead of digestion into singlets, whole genome amplification by random priming may be used to amplify the target before singlets are generated. The rolony treatment and amplification shall ensure that any molecular information obtained by in situ sequencing is not lost during the transfer and before the in vitro sequencing from step g).

As an alternative to the singlets generation by digestion, the rolonies transferred from the tissue may be subjected to PCR amplification using oligonucleotide primers targeting the padlock backbone regions flanking the region of interest. The generated PCR product, encompassing the region of interest and SUMI region, can be circularized and in vitro sequenced.

In the present invention, the padlock technology can be modified to allow spatial localization by SUMI sequencing for other classes of biomolecules. Here, a circular oligonucleotide would be linked to the biomolecule binder. The circular oligonucleotide would contain a SUMI sequence and a coding sequence for the binding principle of the biomolecule (e.g. antibody as binder for proteins). Rolonization of the circular oligonucleotide followed by in situ sequencing of the SUMI and the coding sequence of the biomolecule would allow to obtain spatial multiomics results.

In the present invention the padlocks used in step a) may contain a gene specific coding sequence directly 3' of the SUMI sequence. The sequencing of the SUMI in step e) shall include the gene specific coding sequence. Sequencing of the gene specific coding sequence will allow to determine the targeted nucleic acids by the padlock probes without sequencing into the oligonucleotide region described in step a).

In the present invention the padlocks used in step a) may contain a gene specific coding sequence directly 5' of the SUMI sequence. The gene specific decoding may happen by consecutive hybridization steps using fluorescently labelled probes before or after step e).

In the present invention the padlocks used in step a) may contain two or more sequencing primer designs. Sequential use of the sequencing primers in step e) will allow to increase the rolony sequencing density as optical crowding is avoided.

In the present invention before step e) the formation of the rolony in step d) can be initiated by an external force (e.g. light or heat) which can be linked to a potential digital pathology imaging process.

In the present invention after step e) the cells may be harvested and subjected to single cell sequencing analysis.

The present method combines the use of oligonucleotide forming a padlock while hybridized (padlock probes) where the padlock probe also contains a spatial unique molecular identifier (SUMI) and in situ sequencing of the SUMI to register spatial location followed by sequencing targeted portion of RNA or DNA transcript next to the SUMI at a molecular level in vitro with less limitation in the amount of transcripts and the length of the sequence that can be analyzed.

In this approach, gap-fill padlock probes containing a spatial unique molecular identifier (SUMI) next to the target sequence to capture RNA portion that can be sequenced. Padlock probes have proven very successful in polymerizing short portion of nucleic acids to which it has been hybridized to. Most padlock approaches begin by reverse transcribing the target into cDNA.

The hybridization of the padlock probe to the DNA or RNA strand is followed by a gap-fill step where a reverse polymerase fills the open section between the anchor and the extension side of the padlock from the hybridized 5' portion of the probe using the target mRNA as a guide which is then ligated to from a circular DNA molecule. Alternatively, the padlock can also be hybridized to cDNA which would require additional steps that could be bypassed by targeting the mRNA directly. This technology is known, for example from the already described prior art.

The padlock probes for which the gap has been filled and ligated to form a circular template (the probe can also be filled but ligated only further in the process) are used to code for the SUMI in the actual non hybridizing portion of the padlocks. Finally, the circularized padlock probes are used as a template for rolling circle amplification (RCA) to generate a DNA strand used for sequencing. The thus obtained DNA strands are hereinafter referred to as "rolonies" or "DNA nanoballs".

The current invention describes a method using the gap-fill padlock where the SUMI of the padlock oligomers are used to obtain spatial information and the gap-fill region to obtain target sequence information by sequencing obtained rolonies and/or a combination thereof.

DETAILED DESCRIPTION

Figure 1:
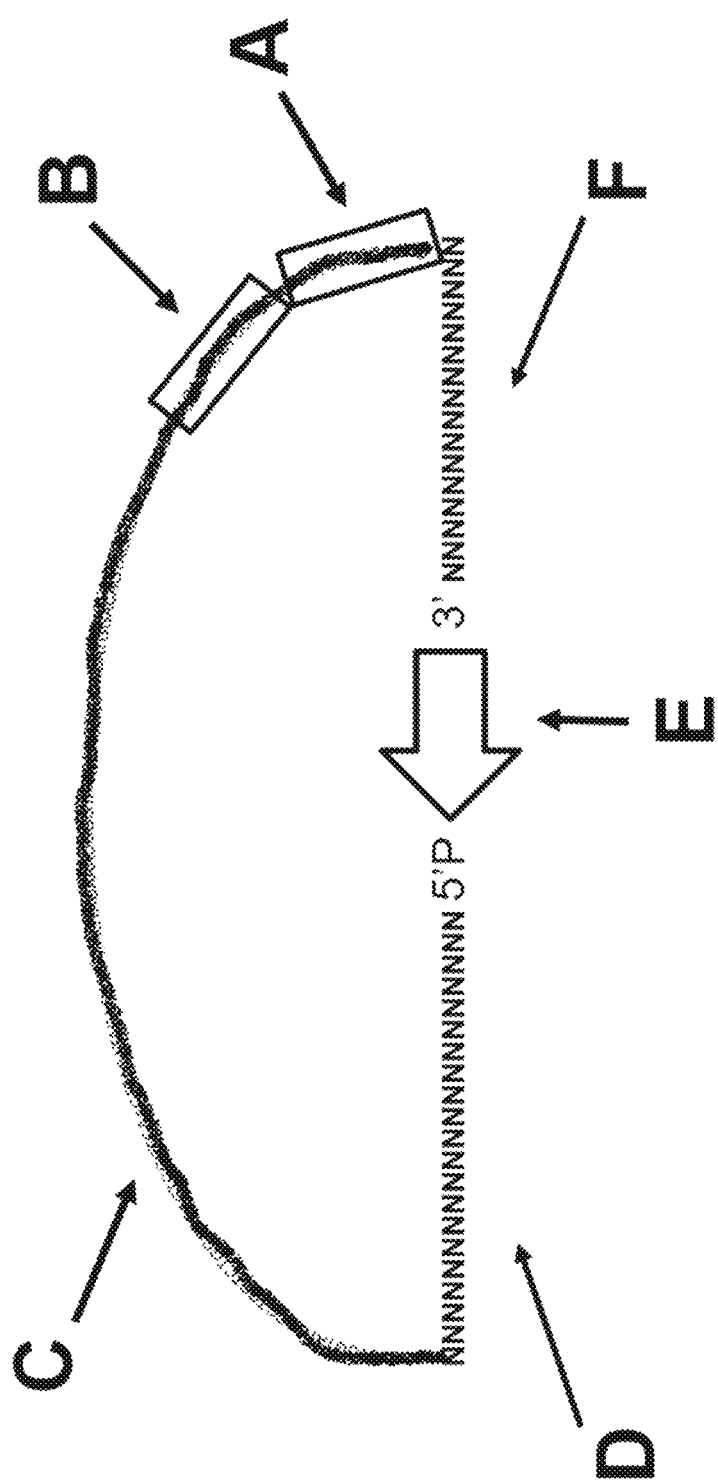
FIG. 1 shows the oligonucleotide padlock design
FIG. 2 shown the Spatial Unique Molecular Identifier (SUMI) sequencing workflow

The method of the invention and its embodiments is further explained referring to the drawings.

FIG. 1 shows the oligonucleotide padlock design with (A) Spatial Unique Molecular Identifier (SUMI) region, (B) Sequencing primer region, (C) Priming regions used for universal amplification 5' end (D) and 3' end (F) region that are complementary to a specific portion of a messenger RNA. (E) Gap region of various length between the 5' and 3' end extremities created by the hybridization of the oligonucleotide creating a padlock-like structure.

FIG. 1. shows an example of a padlock of the invention that can also be used as a template for in situ and in vitro sequencing after generation of the respective rolony. In close proximity to the gap fill target region (E) and the 3' end hybridization region (F) the Spatial Unique Molecular Identifier (SUMI) region (A) and the sequencing primer region (B) is located. For short read in situ sequencing of the rolony by the sequencing primer (B) the SUMI region sequence will be determined. By long read in vitro sequencing of the rolony by the sequencing primer region (B) the SUMI region (A) and in addition the target region (D,E,F) will be determined. The gap region (E) created between the 5' and the 3' end of the padlock may be 0 to 500, preferably less than 200. The core of the padlock i.e. the oligonucleotide may also contain a universal binding site (C) for the binding of a primer used by the polymerase for the rolling circle amplification step (RCA).

Figure 2:
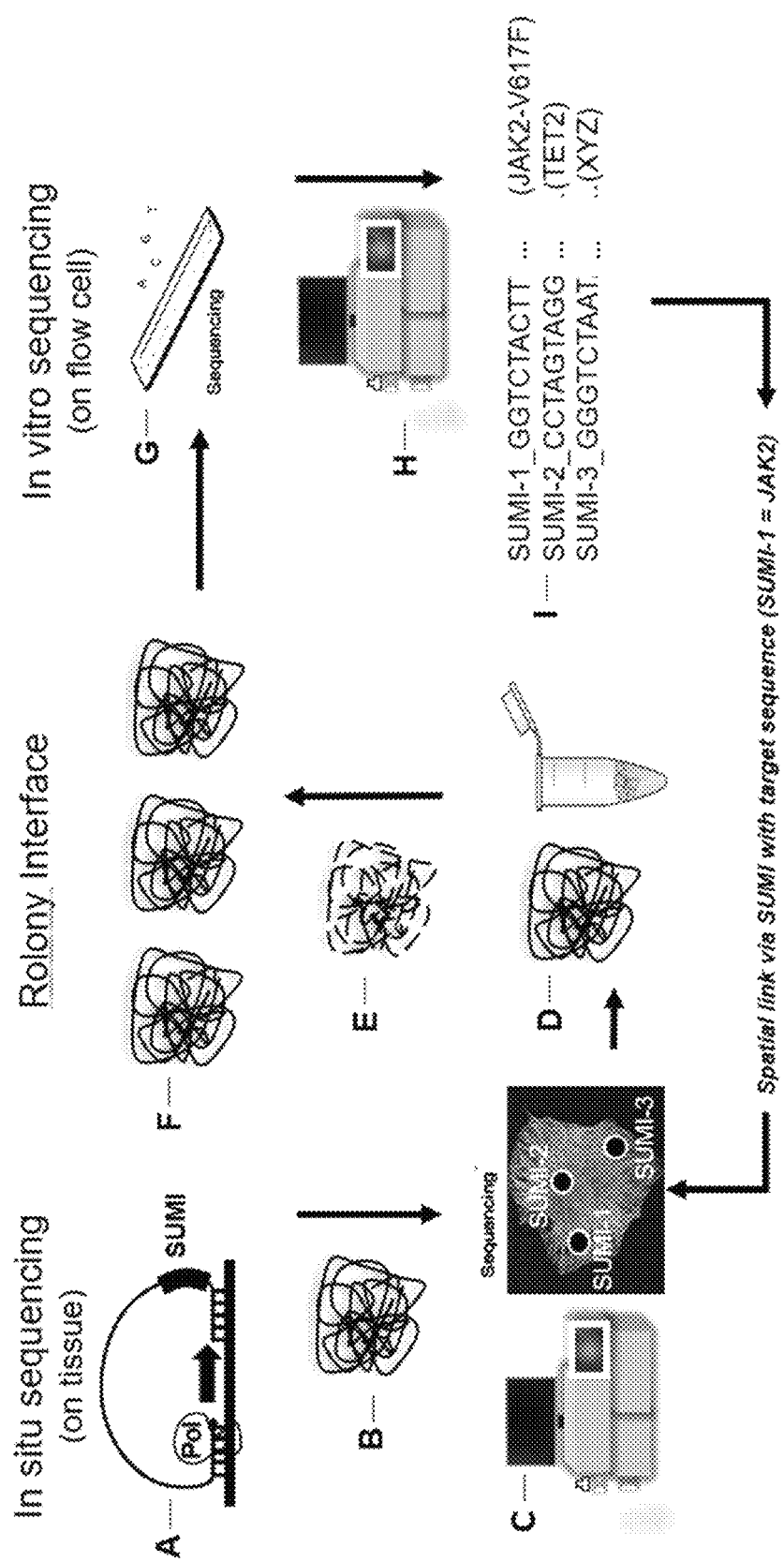

FIG. 2: Spatial Unique Molecular Identifier (SUMI) sequencing workflow for nucleic acid analysis. (A) The gap-fill padlock probe technology using probes that are hybridized to a specific portion of a messenger RNA directly on a section of tissue that has been fixed and permeabilized. (B) Rolony was generated after gap fill ligation to form a circle. (C) The rolony (black dot inside the cell) is sequenced in situ on tissue to derive the SUMI sequence information which is registered spatially (SUMI-1, SUMI-2 and SUMI-3 as examples). Note: only a single cell is shown for illustration. (D) The rolonies are removed from the tissue section and are further processed in vitro. (E) Rolonies are subjected to digestion. (F) Daughter rolonies are generated from the digested nucleic acids. (G) Rolonies are loaded into the flow cell to serve as a template for in vitro sequencing. (G) The flow cell is loaded into the instrument and in vitro sequencing of the rolonies is performed. (H) The sequence information of the SUMI and the target sequence is obtained. The sequence information for the SUMI and the target (JAK2, TET, . . . ) is shown for illustration (I).

FIG. 2 illustrates the baseline workflow for SUMI Sequencing for nucleic acid based analysis. Several modifications are possible. The digestion of the rolonies (E) and the generation of daughter rolonies (F) is optional. Rolonies may directly been transferred from in situ sequencing (D) to in vitro sequencing (G). On the other hand, the digestion of the rolonies may also happen already on the tissue after in situ sequencing (D) which would mean the digested nucleic acids would be starting the in vitro workflow. FIG. 2 also illustrated how the spatial information is obtained by the method described. The SUMI-1 and JAK2 mutation V617F has been obtained by long read in vitro sequencing (I). The SUMI-1 has also been identified spatially within a cell (C).

The combination of both sequencing methods via the SUMI allows the spatial localization of JAK2 V617F, despite the fact that JAK2 V617F has not been sequenced in situ.

Figure 3:
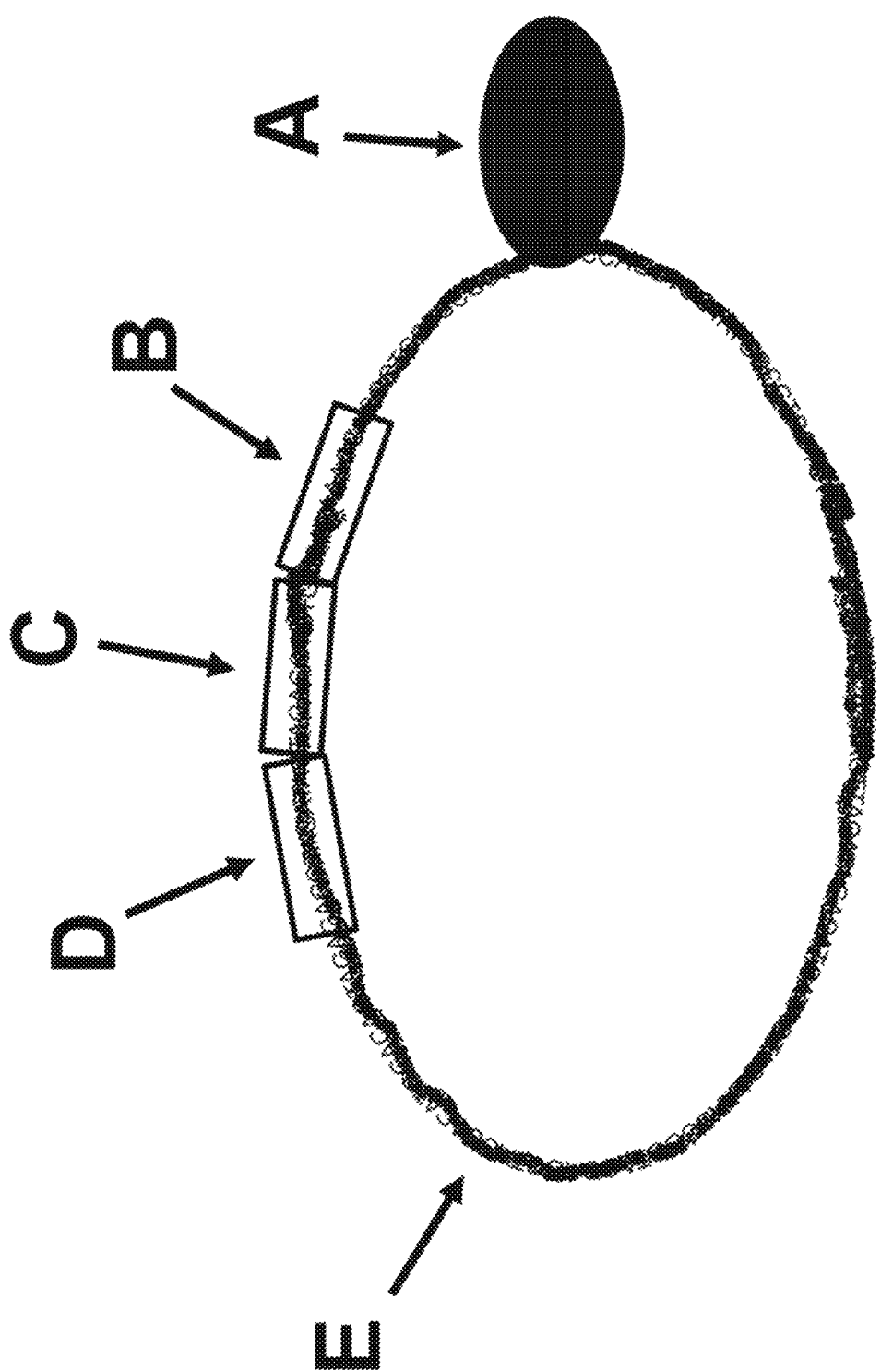
FIGS. 3, 4, 5, 6 and 7 show variants of padlock probes with different sequencing primer designs

FIG. 3. Oligonucleotide design for protein analysis by Spatial Unique Molecular Identifier (SUMI) sequencing workflow. (A) Antibody coupled to circular oligonucleotide. (B) Barcode-Tag region to identify antibody. (C) Spatial Unique Molecular Identifier (SUMI) region (D) Sequencing primer region. (E) Priming region used for universal amplification.

The oligonucleotide may contain 1 to 4 barcode-Tags or barcode regions, each comprising 2 to 20 nucleic acids/nucleotides. If more than one barcode regions is used, the barcode regions have different sequences.

FIG. 3 illustrates an oligonucleotide probe design to spatially identify proteins within a tissue section. The antibody is used to bring the oligonucleotide design for protein analysis to a specific cellular location. The circular oligonucleotide is the template for rolling circle amplification (RCA) by the polymerase after binding of a primer to priming region (E). The resulting rolony is used as a sequencing template on the tissue section for in situ sequencing as described in FIG. 2. Here, the SUMI will be used to identify the spatial location of the protein molecule and by the Barcode-Tag sequence the identity of the antibody and as a result the identity of the protein.

Figure 4:
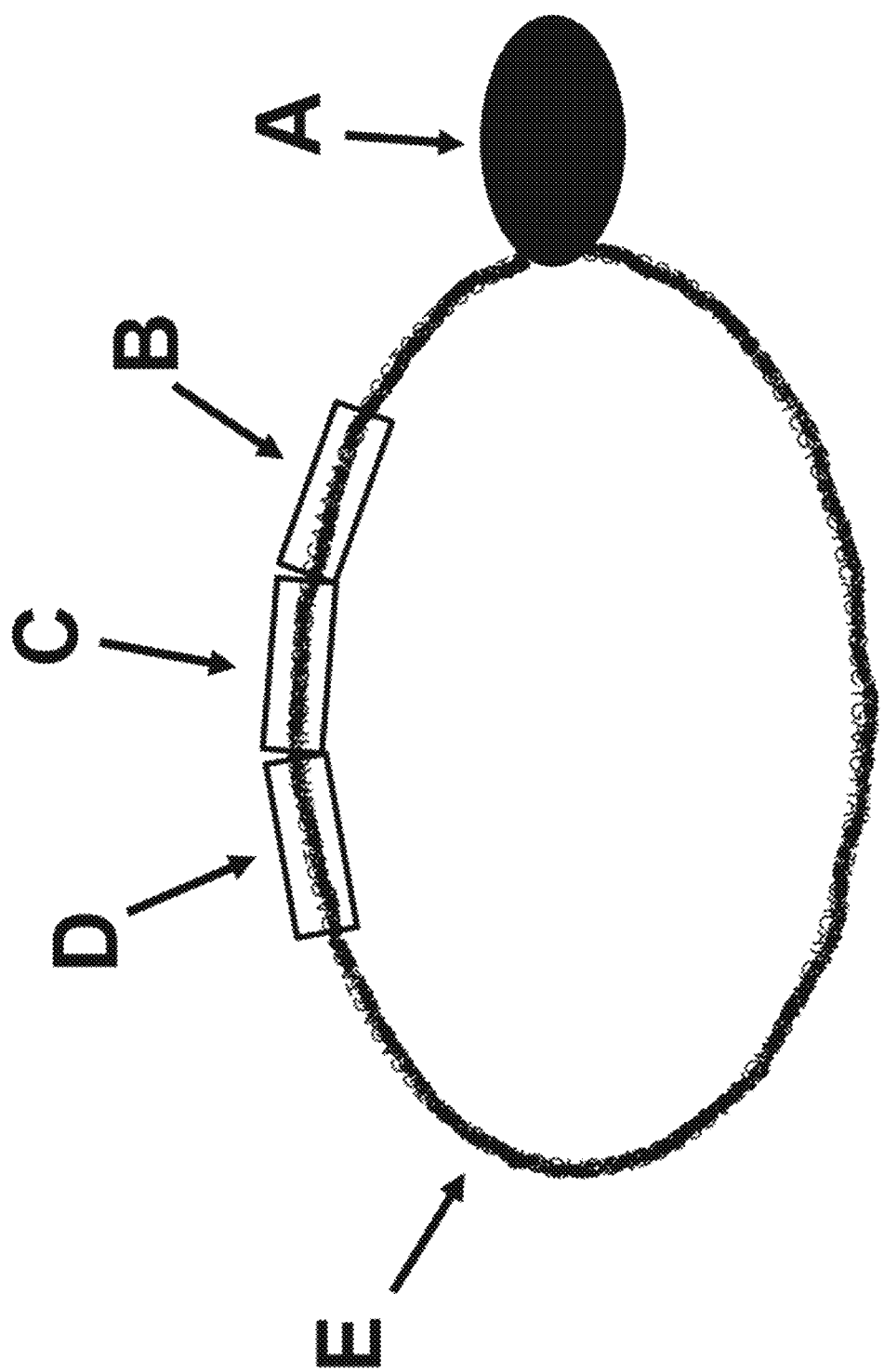

FIG. 4. Oligonucleotide design for molecule analysis by Spatial Unique Molecular Identifier (SUMI) sequencing workflow. (A) Molecule binder coupled to oligonucleotide. (B) Barcode-Tag region to identify molecule binder. (C) Spatial Unique Molecular Identifier (SUMI) region (D) Sequencing primer region. (E) Priming regions used for universal amplification.

FIG. 4 illustrates an oligonucleotide probe design to spatially identify metabolites within a tissue section. A molecule binder is used to bring the oligonucleotide design for the metabolite analysis to a specific cellular location. The circular oligonucleotide is the template for rolling circle amplification (RCA) by the polymerase after binding of a primer to priming region (E). The resulting rolony is used as a sequencing template on the tissue section for in situ sequencing as described in FIG. 2. Here, the SUMI will be used to identify the spatial location of the metabolite molecule and by the Barcode-Tag sequence the identity of the molecule binder and as a result the identity of the metabolite. A typical molecule binder would be streptavidin which binds to Biotin as the metabolite. Biotin can also be coupled to other metabolites to identify their location.

The oligonucleotide probe designs shown in FIG. 1., FIG. 3. and FIG. 4. can be used simultaneously within the Spatial Unique Molecular Identifier (SUMI) sequencing workflow shown in FIG. 2. to provide spatial multiomics analysis of nucleic acids, proteins and metabolites.

Figure 5:
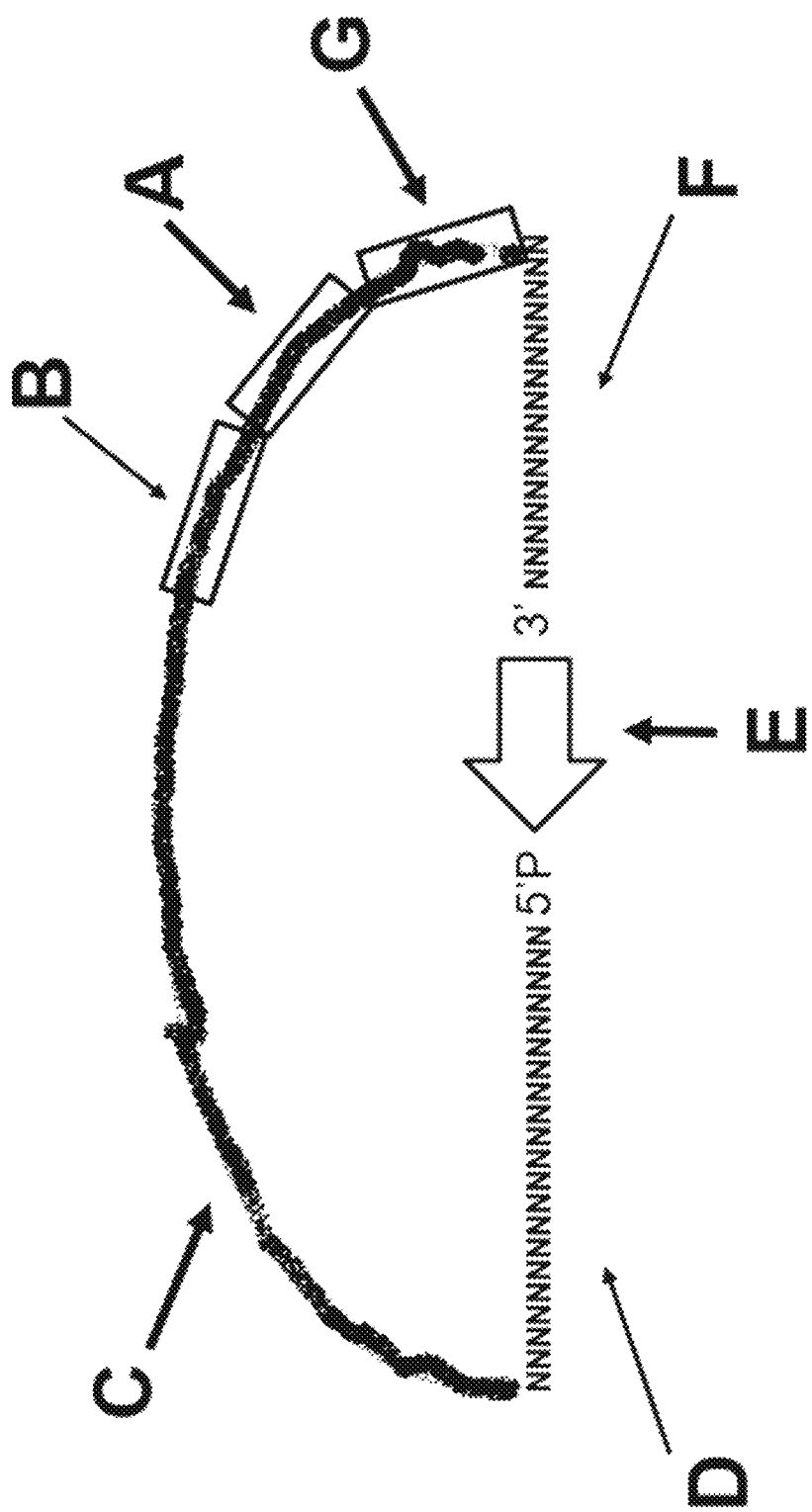

FIG. 5. Oligonucleotide padlock design. (A) Spatial Unique Molecular Identifier (SUMI) region. (B) Sequencing primer region. (C) Priming regions used for universal amplification. 5' end (D) and 3' end (F) region that are complementary to a specific portion of a messenger RNA. (E) Gap region of various length between the 5' and 3' end extremities created by the hybridization of the oligonucleotide creating a padlock-like structure. (G) Barcode-Tag region to identify gene targeted by padlock.

FIG. 5. illustrates an oligonucleotide padlock design which includes a Barcode-Tag region 3' from the SUMI region. By in situ sequencing of the SUMI followed by the Barcode-Tag region the identity of the targeted gene by the padlock is identified. The use of this oligonucleotide padlock design is preferred for the multiomics approach in order to harmonize the required Barcode-Tag in situ sequencing cycles and to allow target identification directly after in situ sequencing.

Figure 6:
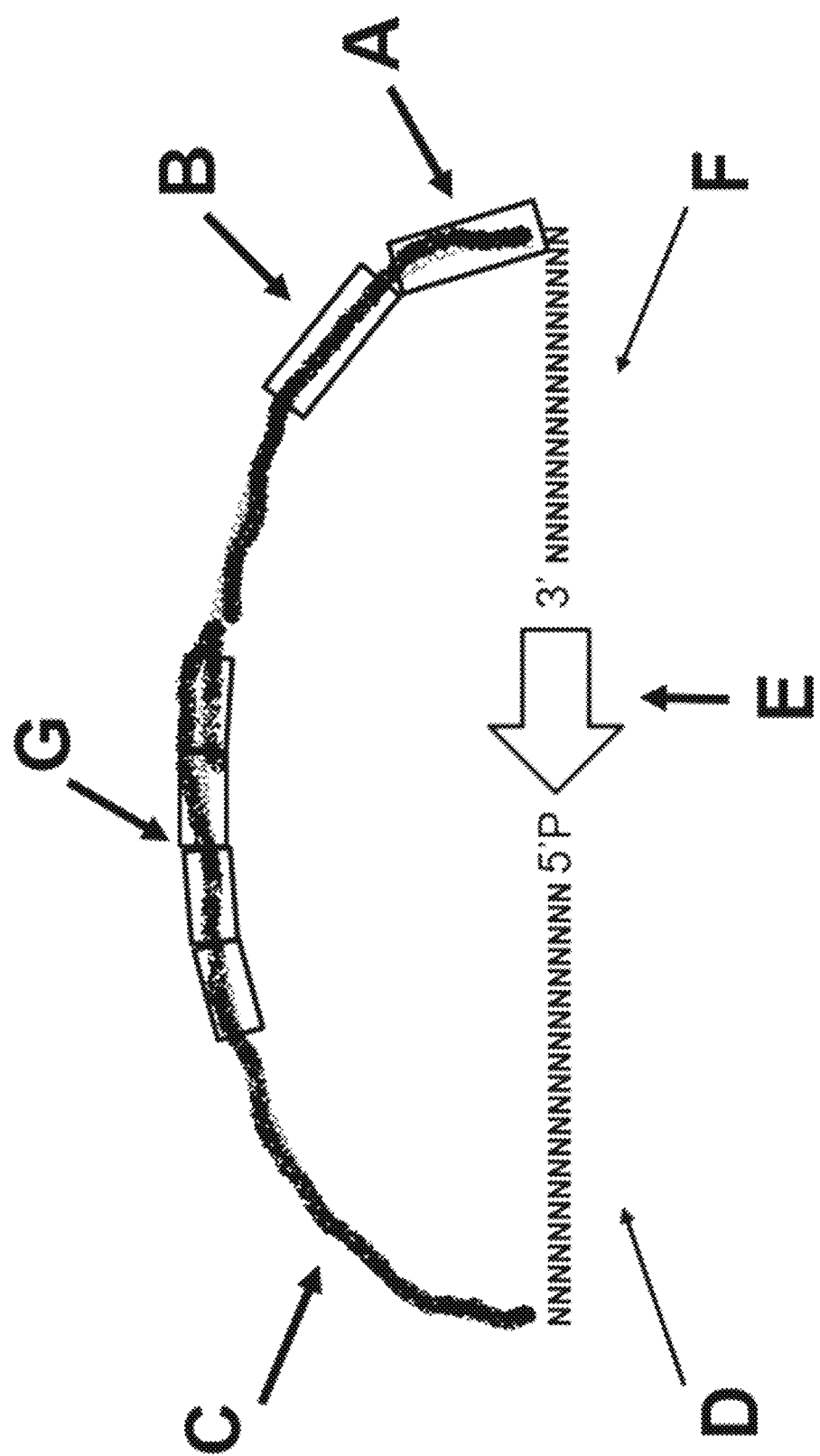

FIG. 6. Oligonucleotide padlock design. (A) Spatial Unique Molecular Identifier (SUMI) region. (B) Sequencing primer region. (C) Priming regions used for universal amplification 5' end (D) and 3' end (F) region that are complementary to a specific portion of a messenger RNA. (E) Gap region of various length between the 5' and 3' end extremities created by the hybridization of the oligonucleotide creating a padlock-like structure. (G) Barcode-Tags to identify Gene targeted by padlock.

FIG. 6. Illustrates a padlock design with includes Barcode-Tag 5' from the SUMI region. Barcode-Tags used as hybridization sites for fluorescently labeled probes to code for the gene targeted by the padlock probe.

Figure 7:
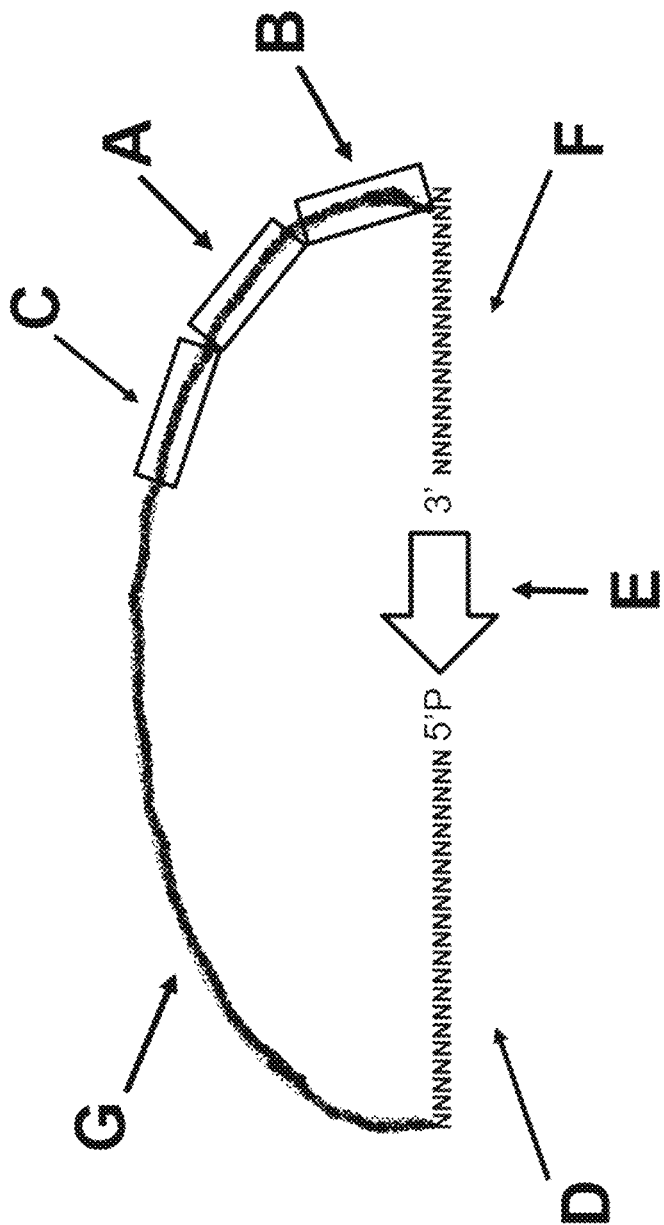

FIG. 7 shows an alternative oligonucleotide padlock design to increase rolony density with (A) Spatial Unique Molecular Identifier (SUMI) region, (B) and (C) Alternative sequencing primer regions. 5' end (D) and 3' end (F) region that are complementary to a specific portion of a messenger RNA. (E) Gap region of various length between the 5' and 3' end extremities created by the hybridization of the oligonucleotide creating a padlock-like structure. (G) Priming regions used for universal amplification.

FIG. 7 shows an example of a padlock of the invention that can be used to increase the density of rolony spots which can be determined by in situ sequencing. The SUMI (A) is sequenced by primer (C) in situ and in vitro. The target region (D,E,F) is sequenced by primer (B) in vitro. Primer C region may have two different sequencing primer designs (C-1 and C-2) representing two subpopulations of the designed padlocks. When sequencing primer C-1 is applied only the rolony subpopulation which matches the padlock C-1 design will be sequenced. As only a fraction of the rolonies light up during fluorescent based sequencing by synthesis, the optical interference between subpopulations C-1 and C-2 is avoided. Sequencing primer for region B is only used for in vitro sequencing allowing longer reads into the target region (D,E,F).

Figure 8:
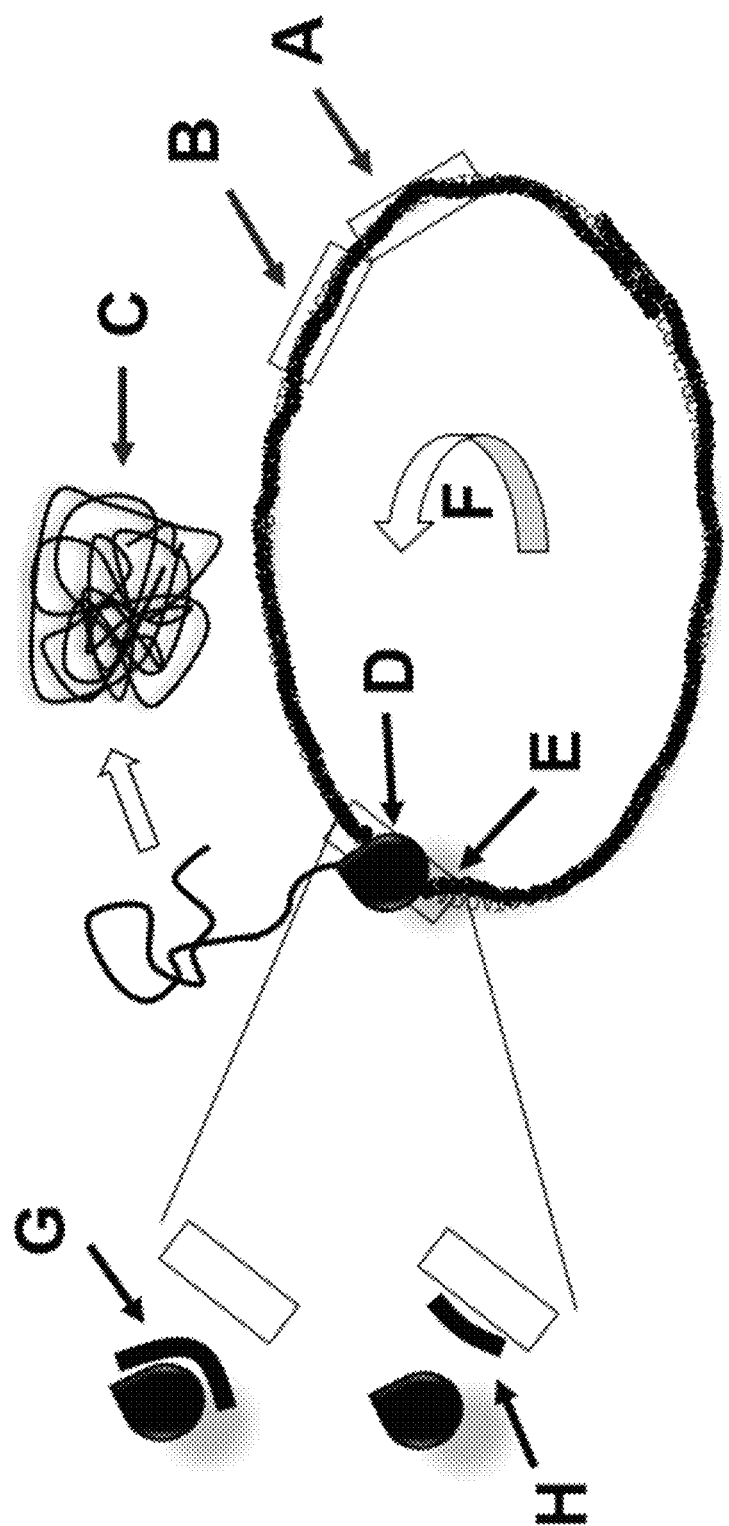
FIG. 8 shows the blocking of rolling circle amplification (RCA) of a circular oligonucleotide.

FIG. 8 Blocking of rolling circle amplification (RCA) of a circular oligonucleotide. (A) Spatial Unique Molecular Identifier (SUMI) region. (B) Sequencing primer region (C). Rolony as a result of RCA reaction. (D) Polymerase to perform RCA (E) Universal primer binding site. (F) Direction of RCA after release of blocker by external force. (G) Blocker binding to polymerase preventing RCA. (H) Blocker binding to universal primer preventing primer binding and initiation of RCA.

FIG. 8 illustrates various methods to prevent rolling circle amplification (RCA) and rolony formation by blocker molecules. The blocker (e.g. an antibody) may be removed by an external force as light or heat. The external force (e.g. light) can be directed by imaging technologies. Imaging technologies can remove the blockers to initiate RCA and rolony generation in areas of interest. As rolony generation is limited to the areas of interest, also sequencing results will only be obtained in the areas of interest.

Padlock Oligonucleotides

As shown in FIG. 1, the oligonucleotide has a 5' and a 3' end recognizing a region of interest comprising around 50-1000 nucleic acids, preferable 50 to 200 nucleic acids and further at least one SUMI comprising a minimum of at least two nucleotides. In the method of the invention, the single strand circular template is replicated by a polymerase capable of rolling circle amplification into a plurality of DNA concatemers forming a DNA nanoball or rolony. For this purpose, the oligonucleotide used in the present invention may comprise at least one primer region with 5 to 50 nucleotides for the rolling circle amplification.

In one embodiment of the invention, the least one primer region is located between the 5' and/or the 3' ends of the oligonucleotide. This embodiment is utilized if the single strand circular template shall be replicated non-selectively using oligonucleotides complementary to the padlock primer region as priming site for the rolling circle amplification polymerase.

In another embodiment of the invention, the least one gene specific Barcode-Tag region (see FIG. 5 and FIG. 6 as examples) is used to identify the gene targeted by the padlock by sequencing or hybridization. The Barcode-Tag region may also be utilized to initiate selective replication by using an oligonucleotides complementary to the barcode region as priming site for the rolling circle amplification polymerase.

In another embodiment of the invention, the SUMIs and the target sequence may have different sequencing primer region allowing that only a subset of the SUMIs are sequenced in situ (see FIG. 7 as example). The sequential use of the sequencing primers allows to obtain a higher rolony density by in situ sequencing.

Circular Oligonucleotides

As shown in FIG. 3 and FIG. 4 circular oligonucleotide may be used for rolony generation. The oligonucleotide designs will include a Spatial Unique Molecular Identifier (SUMI) and a non-nucleic acid based binding principle (e.g. antibody or streptavidin) and a nucleic acid based coding sequence to identify the binding principle. The combination of padlock probes with circular oligonucleotide will allow multiomics analysis to be performed. The Spatial Unique Molecular Identifier (SUMI) sequencing workflow for nucleic acid analysis as shown in FIG. 2 will be expanded for spatial analysis of proteins and metabolites.

Method

In the first embodiment of the invention the padlock probe which contains a Spatial Unique Molecular Identifier (SUMI) as shown in FIG. 1 is used to generate a rolony on a tissue section.

The general steps of the invention are shown in FIG. 2. Here, the gap-fill padlock probe is hybridized to a specific portion of a messenger RNA directly on a section of tissue that has been fixed and permeabilized. The gap-fill region is the sequence of interest on the mRNA, and the gap between the two ends of the probe is filled by the reverse polymerase (POL) from the 5' end using the target mRNA as the guide.

Finally, each extremity of the padlock are ligated creating a circular molecule. The circularized DNA is replicated by a universal primer initiating the rolling circle amplification directly on fixed tissue generating rolonies.

The rolonies serve as sequencing templates for in situ sequencing to identify the Spatial Unique Molecular Identifier (SUMI). The subcellular spatial information for all rolonies are registered and are linked with the SUMI sequence.

After in situ sequencing the rolonies are removed from the tissue section and are directly subjected to in vitro sequencing. It might be preferable to digest the rolonies and to generate daughter rolonies in order to ensure that all in situ sequenced rolonies from in situ sequencing are identified by in vitro sequencing. The digestion of the rolonies may also be performed directly on the tissue section which will support the release of the nucleic acid molecules from the tissue section.

In any case, the rolonies (directly of daughter rolonies) will now be subjected to in vitro sequencing where the Spatial Unique Molecular Identifier (SUMI) followed by the target sequence of interest is determined. As the target sequence is linked to the SUMI sequence from in vitro sequencing and the SUMI spatial subcellular location is known from in situ sequencing, as a result the subcellular location of the target sequence including identified mutations are known as well. With the subcellular location of the mutations, also the cells harboring the mutations across the sequenced tissue section will be revealed.

In the second embodiment of the invention the subcellular location of proteins and metabolites will be revealed by the sequencing workflow. The circular oligonucleotide designs as shown in FIG. 3 will use "antigen recognizing moiety" as a binding principle for proteins to determine the subcellular protein location.

The term "antigen recognizing moiety" refers to any kind of antibody or fragmented antibody or fragmented antibody derivatives, directed against markers expressed on the cells of the cell sample. The term relates to fully intact antibodies, fragmented antibody or fragmented antibody derivatives, e.g., Fab, Fabć, F(abć)2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules. Such antigen recognizing moieties antibody directed may be against antigen expressed by the biological specimens (target cells) intracellular, like IL2, FoxP3, CD154, or extracellular, like CD3, CD14, CD4, CD8, CD25, CD34, CD56, and CD133

For FIG. 4 a circular oligonucleotide design for streptavidin as an example of a binding principle for the metabolite Biotin is shown. The identification of the molecule type will be revealed by sequencing of the Barcode-Tag region to identify molecule binder during the in vitro sequencing step. The Barcode-Tag may also be directly sequenced in situ by extending the read length beyond the SUMI and into the Barcode-Tag region in order to obtain the molecule binder information.

As an additional add on for the second embodiment a padlock design principle for decoding of the targeted nucleic acid is envisioned. The padlock design as shown in FIG. 5. serves as an example of a nucleic acid based spatial analysis where the binding principle is decoded in a Barcode-Tag. Here the in situ sequencing of the Barcode-Tag will identify the targeted gene by reads extending the read length beyond the SUMI and into the Barcode-Tag region, however mutations cannot be identified by this alternative method and longer in situ sequencing reads are required.

As an alternative to the additional add on for the second embodiment a hybridization based decoding principle for the targeted nucleic acid is shown in FIG. 6. This hybridization based method may be advantageous in case a longer in situ sequencing reads beyond the SUMI region cannot be obtained.

In the third embodiment of the invention the spatial resolution of the method shall be improved. In order to improve the spatial resolution, the density of the rolony spots which can be determined by in situ sequencing shall be increased. A padlock design with different sequencing primer designs for SUMI sequencing is envisoned (alternative sequencing primer region (C) is shown in FIG. 7). With the alternative sequencing primers C-1 or C-2 only the respective rolony subpopulation which matches the padlock C-1 and C-2 design will be sequenced. As both rolony subpopulations are optically decoupled by the sequential use of the sequencing primer C-1 followed by C-2, twice as many rolonies can be decoded in the same area. In order to increase the rolony density further additional sequencing primer designs are required (adding design C-3 to increase density 3-fold, etc.). As only a fraction of the rolonies light up during fluorescent based sequencing by synthesis, the optical interference between the rolony subpopulations is avoided.

Rolony subpopulations using different sequencing primers may also be chosen for padlock versus circular oligonucleotide designs to target the spatial analysis of the various molecule classes according to the described invention. In other words the padlock probes (FIG. 1 or FIG. 5) may contain a different sequencing primer designs compared to the circular oligonucleotide designs targeting proteins (FIG. 3) compared to the circular oligonucleotide designs (FIG. 4) targeting metabolites. In this case the sequential use of the sequencing primers will provide sequentially the spatial information of the biomolecules investigated.

In a fourth embodiment the method shall be limited to tissue areas of interest. Tissue areas of interest are identified by classical imaging technologies as microscopy. In order to focus the method of in situ sequencing to the areas of interest, the rolony formation shall be controlled by an external force (as light or heat). As rolonies serve as the sequencing template, without rolonies no sequencing will take place. FIG. 8. summarizes the basic methods to control polymerase activity and applies this principle to the initiation of the rolling circle amplification (RCA) process. Polymerization and initiation of rolony formation may inhibited by blocking the polymerase or by blocking the primer. The blocking principle may be removed by an external force as light or heat which can conceptually be directed by the imaging technologies.

In a variant of this embodiment, after in situ sequencing the tissue section is digested and the individual cells are isolated. The rolony containing cells are sorted and eventually subjected to single cell sequencing. Sorting of the rolony containing cells may be accomplished by the increased nucleic acid content as a result of the rolling circle amplification or by fluorescent intensity derived from hybridization probes directed against the rolony sequence. As the SUMI sequence from in situ sequencing may also be identified by single cell sequencing, the information content from single cell sequencing may be linked to the spatial location via the SUMI derived from in situ sequencing.

In this variant, specific rolonies can be generated from padlocks and circular oligonucleotides by using specific primers corresponding to Barcode-Tag region for targeted gene (see FIG. 5 or FIG. 6) or for the targeted antibody (FIG. 3) or the targeted molecule binder (FIG. 4) to be recognized for example by the Phi29 enzyme used for RCA allowing for the selective amplification of a subset of amplicons. Finally, the sequenced data are linked back to the area on the tissue where the mRNA or cDNA transcripts or the antibodies or the molecule binders of interest interacted with the padlock or the circular oligonucleotide originally.

In this variant, the padlock portion that recognizes a region of interest can also be designed to be more universal for recognizing the 3' portion of mRNA where one of the padlock binding site is composed of poly T, and a 5' side that if composed of random n-mer (random hexamer for instance). The padlock portion that recognizes a region of interest can also be designed to have modified nucleotides such as LNA to help bind the target with higher specificity. The padlock variants may be useful for gene expression analysis, VDJ sequencing of cells of the immune system or identification of lentivirus integration sites.

Samples to be analysed with the disclosed method may originate from any specimen, like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus, Homo sapiens*). A biological sample may have the form of a tissues slice, cell aggregate, suspension cells, or adherent cells. The cells may be living or dead.

The spatial information of the rolonies i.e. the location of the rolonies on the sample is determined for example by an imaging step. In yet another variant of the method according to the invention, the sample is converted into isolated cells which are then immobilized by trapping in microcavities or by adherence.

Imaging may be performed for example with techniques are known as "Multi Epitope Ligand Cartography", "Chip-based Cytometry" or "Multiomics, described for example, in EP 0810428, EP 1181525, EP 1136822 or EP 1224472. In this technology, cells are immobilized and contacted with antibodies coupled to fluorescent moiety. The antibodies are recognized by the respective antigens on the biological specimen (for example on a cell surface) and after removing the unbound marker and exciting the fluorescent moieties, the location of the antigen is detected by the fluorescence emission of the fluorescent moieties. In certain variants, instead of antibodies coupled to fluorescent moieties, antibodies coupled to moieties detectable for MALDI-Imaging or CyTOF can be used. The person skilled in the art is aware how to modify the technique based on fluorescent moiety to work with these detection moieties. The location of the target moieties is achieved by a digital imaging device with a sufficient resolution and sensitivity in for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A method for obtaining a spatial location and sequence information of a target sequence in a sample comprising at least one RNA or c-DNA strand comprising the steps;
    a. providing an oligonucleotide having 50-1000 nucleotides that are complementary to the at least one RNA or c-DNA strand of the sample;
    b. hybridizing the oligonucleotide at its 5' and 3' ends to complementary parts of the at least one RNA or c-DNA strand to create a padlock with a gap between the 5' and the 3' end of the padlock;
    c. filling the gap of the padlock with the complementary nucleotides as target sequence and ligate them to generate a single strand circular template;
    d. multiplying the single strand circular template by a polymerase capable of rolling circle amplification into a plurality of DNA concatemers thereby forming rolonies;
    wherein providing the oligonucleotide with at least one spatial unique molecular identifier (SUMI) comprising at least 2 nucleotides;
    e. determining the spatial location of the rolonies by in situ sequencing of the SUMI;
    f. collecting the rolonies after in situ sequencing and transfer them for in vitro sequencing;
    g. determining the sequence of the SUMIs and the target sequence by in vitro sequencing of the rolonies; and
    h. linking the target sequence of the rolonies with the spatial location obtained from in situ sequencing via the sequence of the SUMIs.

2. The method according to claim 1, wherein the oligonucleotide comprises at least one primer region with 5 to 50 nucleotides for the rolling circle amplification.

3. The method according to claim 1, wherein at least one sequencing primer region is located between the SUMI region and the 5' and/or the 3' ends of the oligonucleotide.

4. The method according to claim 1, wherein rolling circle amplification (RCA) to generate rolonies for in situ sequencing is activated by light and/or heat.

5. The method according to claim 1, wherein after in situ sequencing cells are subjected to single cell sequencing.

6. The method according to claim 1, wherein the oligonucleotide comprises at least one barcode-tag comprising at least 2 nucleotides.

7. The method according to claim 1, wherein the rolony transfer includes nucleotide fragmentation and/or targeted enrichment and/or amplification.

* * * * *